(12) United States Patent
Hofmann et al.

(10) Patent No.: US 6,429,208 B1
(45) Date of Patent: Aug. 6, 2002

(54) METHODS AND COMPOSITIONS FOR RESTORING IMPAIRED CELLULAR IMMUNE FUNCTION

(75) Inventors: Bo Hofmann; Parunag Nishanian, both of Los Angeles; John L. Fahey, Pacific Palisades, all of CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 07/859,572

(22) Filed: Mar. 27, 1992

(51) Int. Cl.7 .................... A61K 31/52; A61K 31/38
(52) U.S. Cl. ................... 514/263; 514/264; 514/934; 514/431
(58) Field of Search ................ 514/263, 264, 514/934, 431

(56) References Cited

U.S. PATENT DOCUMENTS 4,861,759 A * 8/1989 Mitsuya et al. ............... 514/46

OTHER PUBLICATIONS

Legrand et al, Biochemical Pharmacology vol. 40(5)p–1103–1109, 1990.*
Ahluwalia et al 108 CA:31396m 1988.*
Herdewijn et al 107 CA: 176403a 1987.*
Van Aerschot et al 111 CA: 58257R 1989.*
Haurmenberg et al 115 CA: 150368h 1991.*
Legrand et al 113CA:185172a 1990.*

* cited by examiner

Primary Examiner—Russell Travers
(74) Attorney, Agent, or Firm—Morrison & Foerster LLP

(57) ABSTRACT

The effect of HIV components on lymphocytes, as exemplified by peripheral blood mononuclear cells (PBMC) in retarding their proliferation can be reversed by inhibiting the PKA/cAMP pathway. By using protocols which inhibit this pathway, the ability of lymphocytes to proliferate can be restored. The restoration of this pathway is useful in reversing the effects of HIV infection.

8 Claims, 14 Drawing Sheets

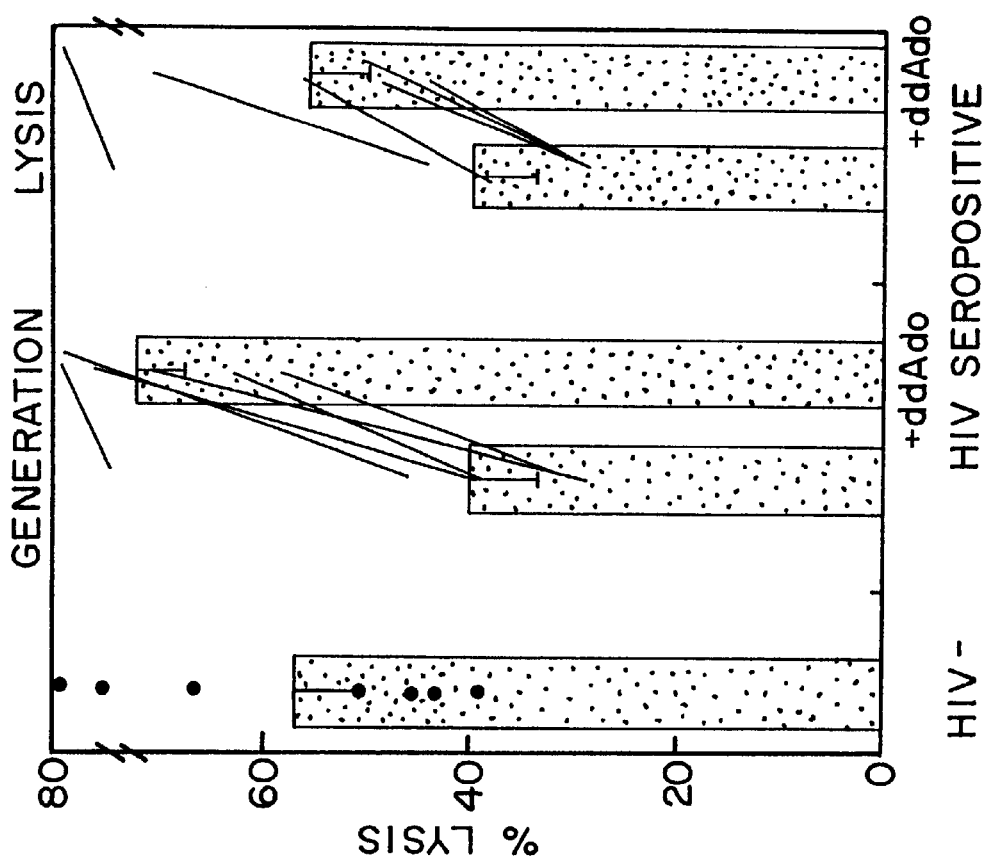
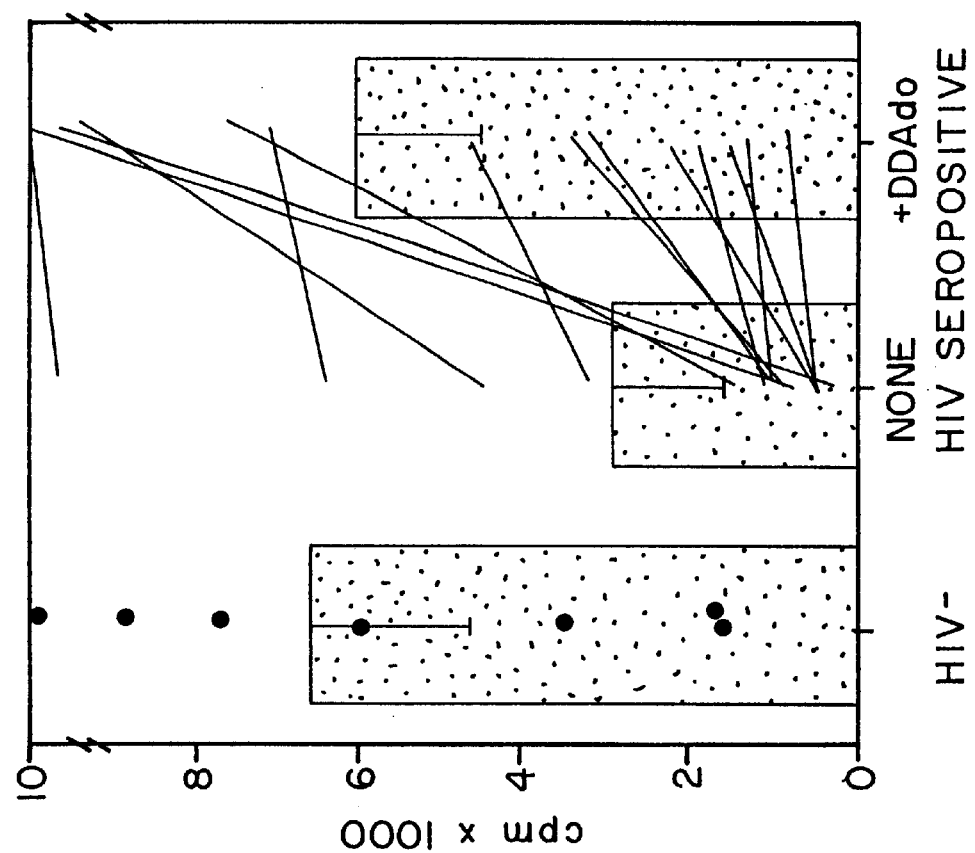
FIG. 10A
FIG. 10B

METHODS AND COMPOSITIONS FOR RESTORING IMPAIRED CELLULAR IMMUNE FUNCTION

Portions of the work leading to this application were developed under a grant of the National Institutes of Health under Grant No. AI-23606. The NIH may have rights in this application.

TECHNICAL FIELD

This invention relates generally to the use of therapeutic agents to regulate immune function. More specifically, this invention relates to the use of inhibitors of the PKA/cAMP pathway to restore T-cell proliferation and to improve immune function impaired in patients infected with Human Immunodeficiency Virus (HIV).

BACKGROUND

HIV infection leads to immunological disregulation, dysfunction, and abnormalities that result in the development of AIDS. Although less than 1% of lymphocytes are infected with HIV, the vast majority of lymphocytes demonstrate defective function. Drugs, such as AZT, currently approved for treatment of HIV infection, are aimed at inhibiting viral replication rather than restoring defective immune function.

It has been shown that lysates of HIV are capable of impairing proliferation of normal peripheral blood mononuclear cells (PBMC). Pahwa, S., et al., *Proc Natl Acad Sci USA* (1985) 82:8198–8202, showed that a disrupted HTLV-III viral preparation in relatively dilute concentrations stimulated immunoglobulin secretion by peripheral blood lymphocytes, but at the same dosages was inhibitory for B-cell differentiation responses induced by polyclonal B-cell activators. More recently, Hofmann, B., et al., *Cell Immunol* (1989) 121:336–348, showed that detergent-disrupted HTLV-IIIB lysate exerted a strong suppressive effect on PHA-stimulated lymphocytes, although the lysate was not directly cytotoxic to lymphocytes and did not contain tumor necrosis factor or lymphotoxin. It was shown that the lysate specifically suppressed the proliferation of a range of hematopoietic cell lines. Thus, it is clear that live virus is not necessary to inhibit the proliferation of PBMC.

In a more recent paper, Hofmann, B., et al., *J Immunol* (1990) 145:3699–3705, showed that inactivated HIV inhibited the phosphatidyl inositol-4,5-biphosphate and phosphatidic acid-mediated mechanisms of cell activation. This paper showed that treatment of mononuclear cells with inactivated HIV resulted in a decreased inositol phospholipid turnover, leading to a decreased generation of diacyl glycerol (DAG), presumably interfering with phosphokinase C (PKC) activation. As PKC is required for proliferation, presumably diminution of the PKC concentration would result in reduced proliferation, which was also demonstrated in the Hofmann paper. The paper also shows that the expression of receptors for IL-2 and transferrin is decreased.

An alternative mechanism for diminished PKC activity involves stimulation of phosphotyrosine kinases (PTKs), which, in conjunction with the secondary messenger, cyclic AMP, stimulates phosphokinase A activity. Elevated phosphokinase A (PKA) activity is known to inhibit PKC.

As shown hereinbelow, proteins derived from HIV are able to activate this pathway. HIV components induce a signal in T lymphocytes which leads to activation of several protein tyrosine kinases (PTK) in both CD4 and CD8 cells. This is followed by induction of protein kinase A (PKA) and an increase in intracellular cAMP concentrations, which are necessary for the activation of PKA.

Accordingly, the invention is directed to methods to stimulate the proliferation of PBMC so as to ameliorate the effects of AIDS infection. These methods include treating T-lymphocytes by administering medicaments which inhibit HIV-induced increases in cAMP/PKA activity. Increased cAMP/PKA activity results in changes that impair proliferation when cells are stimulated with phytohaemagglutinin (PHA), including lowered membrane protein kinase C (PKC) activity.

One set of agents relevant to such inhibition is directed to adenylate cyclase. A number of inhibitors of adenylate cyclase, the enzyme required for the formation of CAMP, are known, including the Chinese herb extract "dan-shen".

Some of these inhibitors have been used as antivirals. For example, U.S. Pat. No. 4,861,759 discloses compositions containing 2',3'-dideoxyadenosine, 2',3'-dideoxyinosine, and dideoxyguanosine and their triphosphates for use in treating retroviral infections.

Nokta et al. (*Virology* 181:211–217, 1991) demonstrated that HIV infection of MT-4 and other tumor cells was associated with an increase in intracellular levels of cAMP and cGMP. These results are different from those reported hereinbelow in that the target cells were exclusively tumor cell lines, and the elevation in levels of cAMP and cGMP were detected only after very long periods—i.e., five days after infection. Importantly, the work described in this article has to do with direct viral infection rather than viral lysates; indeed, when a "control" using contact with viral protein was tested, there was no detectable increase in cAMP or cGMP levels after five days. Accordingly, Notka concluded that live virus was required to elevate the levels of these cyclic nucleotides.

In an abstract published in connection with the Sixth Annual Conference on Clinical Immunology, Nov. 1–3, 1991, the present inventors disclosed that HIV components induced a signal into T lymphocytes which led to the activation of several PTKs in both CD4 and CD8 T-cells. By use of the specific inhibitor Tyrphostin 25, it was shown that PTK activity was responsible for subsequent induction of PKA, which was, also, accompanied by an increase in intracellular cAMP, necessary for activation of PKA. The inventors herein concluded in this abstract that HIV-induced increased cAMP/PKA activity resulted in changes that impaired proliferation when cells were subsequently stimulated with PHA, including lowering the levels of membrane PKC. A specific inhibitor of PKA (H89) was successful in increasing PKC activity. However, bromo-cAMP and cholera toxoid, reagents which augment intracellular cAMP, resulted in decreased PKC activity.

DISCLOSURE OF THE INVENTION

The present invention concerns methods and compositions for enhancing the function of peripheral blood mononuclear cells (PBMC), thus sustaining the ability of the immune system to provide suitable functionality. This is of particular importance in subjects infected with HIV, since the viral components, not necessarily live viruses, are sufficient to inhibit lymphocyte, especially PBMC, proliferation and impair function. The methods of the invention are directed to protocols that inhibit the PKA/cAMP pathway.

BRIEF DESCRIPTION OF THE DRAWINGS

FIG. 10A is a graph showing that proliferative responses of PBMC from HIV seropositive subjects to a specific recall antigen (*Candida albicans*) are increased by treatment with ddAdo. FIG. 10B is a graph showing that ddAdo increases the ability of cytotoxic T-cells from HIV seropositive subjects to lyse allogenic cells.

DETAILED DESCRIPTION OF THE INVENTION

Figure 1:
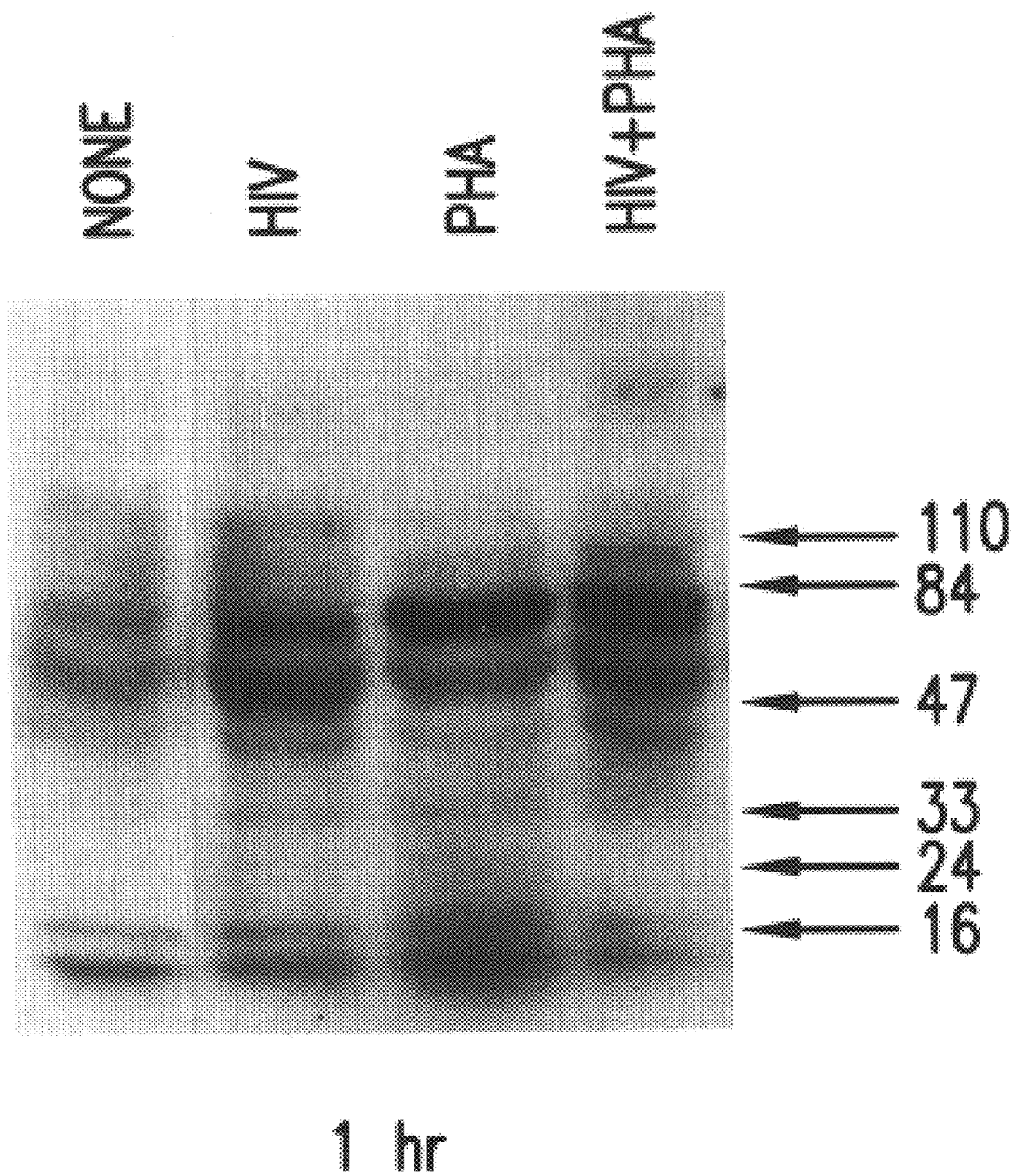
FIG. 1 is a half-tone photograph of a Western blot visualizing phosphorylated protein tyrosine residues as a result of induction of PTK activity by HIV components or PHA added to normal PBMC in vitro.

The methods and compositions of the invention employ inhibitors of the PKA/cAMP pathway. This established pathway for inhibiting cell proliferation is believed to result, for example, in response to simulation by PHA. In response to this stimulation, phosphotyrosine kinases (PTKs) are activated which in turn may induce elevation of protein kinase A (PKA) levels. PKA is an enzyme which requires cyclic AMP (cAMP) for activity; cAMP is produced by the action of the enzyme adenylate cyclase. Thus, the combination of PKA/cAMP is required for further effect of this pathway. The activated form of PKA diminishes the membrane activity of protein kinase C (PKC). The membrane bound activity of PKC is known to be required for cell proliferation. Thus, it is known that increased cAMP/PKA activity in T lymphocytes inhibits the proliferation promoter, protein kinase C (PKC) (Kammer, *Immunol Today* (1988) 9:222–9; Droge, *Immunol Today* (1986) 7:340–3). Normal PKC activity is necessary for T lymphocyte functions such as proliferation and cytotoxicity (Darryl, et al. *J Immunol* (1990) 145:449–55; Takayama, et al., *J Biol Chem* (1988) 263:2330–2336; Sitkovsky, et al. *Annals NY Acad Sci* (1988) 532:350–358). "Inhibition of the cAMP/PKA pathway" refers to methods and compositions which diminish the levels or activity of PKA and/or cAMP. This can be done, for example, by inhibiting the activity of adenylate cyclase, by decreasing the levels of PKA, by decreasing the levels of adenylate cyclase, by inhibiting the activity of PKA, or by inhibiting one or more of the PTK enzymes that may be involved in activation of PKA.

"Treating", as used herein, shall mean (1) providing a patient with an amount of a substance sufficient to act prophylactically to prevent the development of a weakened and/or unhealthy state; or (2) providing a subject with a sufficient amount of a substance so as to alleviate or eliminate a disease state and/or the symptoms of a disease; weakened and/or unhealthy state.

"Antiviral agents" refers to agents which affect the infection of host cells, replication, integration, or expression of viral nucleic acid, the activity of viral gene products, or the production of infectious virus particles.

Inhibitors of adenylate cyclase may be agents which reduce adenylate cyclase activity by any mechanism, including, but not limited to, competitive, non-competitive, and uncompetitive inhibitors of enzyme activity, agents which prevent the expression of the adenylate cyclase gene, and antagonists of adenylate cyclase. One inhibitor of adenylate cyclase is the extract of the Chinese herb *Saliera miltirrhiza* dan-shen and active constituents, polyphenolic acid, rosemurinic acid, litospermic acid, and their methyl ester derivatives (Kohda et al., *Chem Pharm Bull* (1989) 37:1287–1290). Additional examples of inhibitors are polyadenylates and adenosine phosphates. For example, U.S. Pat. No. 3,810,883 discloses 2'-O-palmitoyladenosine 3'-5'-cyclic monophosphate and $N^6$, 2'-o-dipalmitcyladenosine-3'-5'-cyclic monophosphate as potent inhibitors of adenylate cyclase; U.S. Pat. No. 4,678,853 discloses 1-benzyl-2-(N-substituted)-carbamoyl-tetrahydroisoquinoles which are inhibitors of adenylate cyclase.

In an additional approach, the levels of cAMP may be diminished by enhancing the levels of phosphodiesterase which catalyzes the decomposition of cAMP. These levels may be enhanced, for example, by addition of expression systems for this protein.

Alternative to modulating the levels of cAMP directly or indirectly, inhibitors which affect the catalysis by enzyme protein kinase A or protein tyrosine kinases may also be used. At the present time, the most specific of the known PKA inhibitors is H-89. Other less specific PKA inhibitors are known and may be used, although inhibitors that also significantly inhibit PKC should be avoided. Inhibitors of the PTK family of enzymes include the tyrophostin series, which are numbered from 1 to greater than 25. Tyrophostin-23 and tyrophostin-25 are the compounds more specific for PTKs than for other enzymes.

In general, then, the protocols which inhibit the PKA/cAMP pathway include treatment of the cells to be targeted, either in vitro or in vivo, including extracorporeal methods for in vivo treatment, with inhibitors of the elements of this pathway or their precursors.

In addition to supplying inhibitors of adenylate cyclase activity, the amount of adenylate cyclase present may be reduced by inhibiting the production thereof using, for example, antisense technology. Thus, the complement to mRNA encoding adenylate cyclase may be supplied by providing an expression system to the target cells for this complement. Typically, such expression systems are constructed by inserting the gene encoding adenylate cyclase into the expression system in the reverse orientation. Alternatively, the DNA portions encoding adenylate cyclase may be inhibited directly using agents which bind directly to this duplex DNA.

Pharmaceutical formulations of the invention which include inhibitors of the PKA/cAMP pathway for administration to patients or for use in extra corporeal treatment will generally include an amount of the inhibitor effective to inhibit this pathway, and optionally, an anti-viral agent, in addition to a pharmaceutically acceptable excipient. Suitable excipients include most carriers approved for parenteral administration, including water, saline, Ringer's solution, Hank's solution, and solutions of glucose, lactose, dextrose, ethanol, glycerol, albumin, and the like. These compositions may optionally include stabilizers, antioxidants, antimicrobials, preservatives, buffering agents, surfactants, and other accessory additives. A presently preferred vehicle comprises about 1 mg/ml serum albumin (species-specific) in phosphate-buffered saline (PBS). A thorough discussion of suitable vehicles for parenteral administration may be found in E. W. Martin, "Remington's Pharmaceutical Sciences" (Mack Pub. Co., current edition sections relating to the excipient vehicles and formulating being incorporated herein by reference to disclose such). Such formulations are generally known to those skilled in the art and are administered systemically to provide systemic treatment.

The precise dosage necessary will vary with the age, size, sex and condition of the subject, the nature and severity of the disorder to be treated, and the like; thus, a precise effective amount cannot be specified in advance and will be determined by the care giver. However, appropriate amounts may be determined by routine experimentation with animal models, as described below. In general terms, an effective dose of ddAdo for systemic treatment will range from about 1 mg to about 50 mg per kg of body weight. Effective doses for 3'-AMP and 2',3'-AMP are in the same range.

Suitable anti-viral agents that may be used in combination with inhibitors of adenylate cyclase include AZT, ddC and ddI.

EXAMPLES

The following examples illustrate the compositions and methods of the invention and do not limit its scope.

Example I

Induction of Lymphocyte Protein Kinases

A. General Methods

1. Cell Cultures

Peripheral blood mononuclear cells (PBMC) from healthy blood donors were isolated by Lymphoprep (Nyegaard and Co., Oslo, Norway) density gradient centrifugation. Cell cultures were prepared in Eppendorf tubes and contained $5-10\times10^6$ cells/ml for phosphotyrosine experiments and $2-5\times10^6$ cells/ml for the kinase experiments and the cAMP determinations described below. The concentration of PHA added per tube was 10 µg/ml of PHA-P (Wellcome, Beckenham, England). Phorbol 12 myristate-13 acetate (PMA) (P-8139, Sigma, St. Louis, Mo.) was dissolved in dimethylsulfoxide (DMSO) and used in optimal concentrations of 200 ng/ml. The total volume per tube was 1 ml.

Proliferative assays were performed as previously described (see, for example, Hofmann, B., et al., *Cell Immunol* (1989) 121:336–48. Briefly, one microcurie $^3$H-thymidine was added to cultures 72 hours after stimulation, and after further 24 hours, all cultures were harvested on glass fiber filters with an automatic harvesting machine (Skatron, Lierbyen, Norway), and the incorporated radioactivity was measured in a liquid scintillation counter (Beckman LS 1800) after an addition of 1.5 ml scintillation fluid.

The concentration of the following inhibitors which resulted in 50% inhibition of cell proliferation was determined in initial experiments. The concentration of Cholera toxoid was 10–0.2 µg/ml and 8-bromoadenosine 3',5' cyclic monophosphate (Br-cAMP) was 40–0.2 µg/ml. H-89 has a 660 fold higher affinity for PKA than for PKC. The PTK inhibitor Tyrphostin 25 (Bimol, Plymouth, Pa.) was used in a concentration of 1.0 µg/ml. Tyrphostin 25 has more than 30 fold higher affinity for PTK than for PKC and PKA. HIV components were added to final dilutions of 108–360 µg p24 antigen/ml.

2. Virus Preparation

Methods for HIV preparation and inactivation previously described (Hofmann, B., et al., *J Immunol* (1990) 145:3699–705. Briefly, virus was prepared from the supernatants of infected cell lines by a first centrifugation to remove cell debris, filtration through an 0.45 micron filter, and a final centrifugation of the filtrate to pellet the virus. Inactivated virus was similarly prepared by adding 0.1 volume of 0.5 M Tris-HCl, pH 7.5, and 0.015% (v/v) β-propiolactone (BPL) after removal of cell debris, and incubating at room temperature shielded from light for 24 hours. The inactivated virus was then pelleted by centrifugation. Preparations may be quantitated by measuring the amount of HIV core protein by ELISA (DuPont/NEN Research Products, Wilmington, Del.). The final concentration of HIV components in cultures were 108–360 pg p24 antigen/ml. Other HIV strains and inactivation methods have earlier been tested and shown to have similar inhibitory effects.

3. Purification of T Lymphocyte Subsets

T-cell subsets were purified by depleting T-cells, prepared by sheep red blood cell resetting, for either CD4 or CD8 T-cells as described by Hofmann, B. et al., *J Immunol*, supra. Briefly, monoclonal antibodies to CD4 or CD8 cells (Ortho-Immune, Raritan, N.J.) were added to pelleted PBMC. After incubation for 30 minutes at 40° C., BioMag (iron particles coupled to goat anti-mouse antibodies, Advanced Magnetics, Inc., Cambridge, Mass.), was added and the sample agitated for 30 minutes at 4° C. The suspension was then placed on a flat magnet for two minutes, after which the supernatant containing the remaining cells is removed. After washing the cells, free beads were removed by layering the suspension on top of undiluted Percol (Pharmacia, Uppsala, Sweden) and centrifuging the free beads to the bottom of the tube.

Attempts to use positively selected cells were unsuccessful because of preactivation during preparation.

4. Phosphotyrosine Determinations

After activation, the PBMC were spun down and lysed with 100 μl per 12×10⁶ cells of lysing buffer (It Triton X, 5 mM Tris, 5 mM EDTA, 10 nM sodium vanadate, 100 μg/ml phenylmethylsulfonyl fluoride) and sonicated three times for 10 seconds with 50 watts on ice. The cell lysates were then run on a precast 4–20% gradient SDS PAGE and electroblotted to a nitrocellulose membrane. After blocking with BSA as inert protein, the membrane was incubated with a monoclonal antiphosphotyrosine antibody (Sigma) for three hours. After washing, the membrane was probed with an $^{125}$I-labeled goat-anti mouse antiserum (ICN, Irvine, Calif.), for 2 hours and washed. An X-ray film (Kodak, Rochester, N.Y.) was then exposed to the membrane for 1–3 days. The bands were identified according to the film, cut out of the membrane, and counted in a gamma counter. Antiphosphotyrosine monoclonal antibody purchased from another company (Boehringer Mannheim) gave similar results.

5. PKC Determinations

The reagents were obtained as a kit from Gibco (Grand island, N.Y.) and the manufacturer's protocol was followed. After activation, cell membrane fractions were then obtained by ultracentrifugation (100,000 g for one hour at 4° C.) of sonicated cell lysates without detergent. Membrane fractions were then sonicated in the presence of 0.05% Triton X and the specific PKC activities were determined. Specific PKC activity was determined as the difference between phosphorylation of a PKC specific substrate with and without a specific PKC inhibitor present. The specific PKC substrate was a synthetic peptide from myelin basic protein with an acetylated N-terminal glutamine. The specific PKC inhibitor was a pseudo-substrate peptide which specifically binds to the pseudo-substrate region of the regulatory domain of PKC. The reaction mixture was spotted on cellulose paper, non-bound $^{32}$P-ATP was removed by washing, and the paper discs were counted in a β counter after addition of scintillation fluid. The amounts of lysate over which the assay was linear were determined in initial experiments. All experiments were repeated 2–5 times.

6. PKA Determinations

The reagents were obtained as a kit from Gibco and the manufacturer's protocol was followed. After activation, cells were sonicated, and the specific PKA activity in the cell lysates were assayed. Specific PKA activity was determined as the difference between phosphorylation of a PKA specific substrate with and without a specific PKA inhibitor present. The specific PKA substrate was a synthetic peptide "leu arg arg ala ser leu gly (SEQ ID NO:1), also called "kemptide." The specific PKA inhibitor was a synthetic peptide called "PKI" which was an alanine to serine replacement in the "consensus sequence" "X arg arg X ser X (SEQ ID NO:2)," were X is any amino acid, which specifically binds to the pseudoregion of the regulatory domain of PKA. The reaction mixture was spotted on cellulose paper discs and counted as described for PKC. All experiments were repeated 2–5 times.

7. cAMP Determinations

This assay is a commercial scintillation proximity RIA (Amersham, Arlington Heights, Ill.) and the manufacturer's protocol was followed.

B. HIV Components Induce Sustained Phosphorylation of Protein Tyrosine Residues in Normal PBMC Because the activity of protein tyrosine kinases (PTK) is low in resting T lymphocytes, increased PTK activity is a good indicator of cell activation.

When HIV components or PHA was added to normal PBMC for one hour in vitro as described above, PTK activity was induced. This induction of PTK activity was demonstrated by the generation of phosphorylated protein tyrosine residues visualized on a Western blot after PAGE separation of lysates of the cells (FIG. 1). Phosphotyrosine was detected in protein bands from about 10–200 kD, indicating activity of various PTKs. Three bands of about 40, 55, and 80 kD were particularly strong. These bands were used to quantify activity.

As shown in the left lane, low levels of phosphotyrosine were detectable in non-stimulated PBMC kept under the same conditions as stimulated PBMC.

C. Protein Tyrosine Kinase Activity Induced by HIV Components Can Be Measured as Early as Five Minutes After Stimulation Addition of HIV components to normal PBMC induced bands similar to those induced by PHA. Pre-exposure of normal PBMC to HIV components for 10 minutes followed by PHA activation for one hour did not increase or decrease subsequent PHA induced generation of phosphotyrosine. Similar data were obtained after 2 hours of stimulation. Thus, HIV components actively induced signals in normal PBMC, and sustained intracellular changes are generated.

Figure 2A:
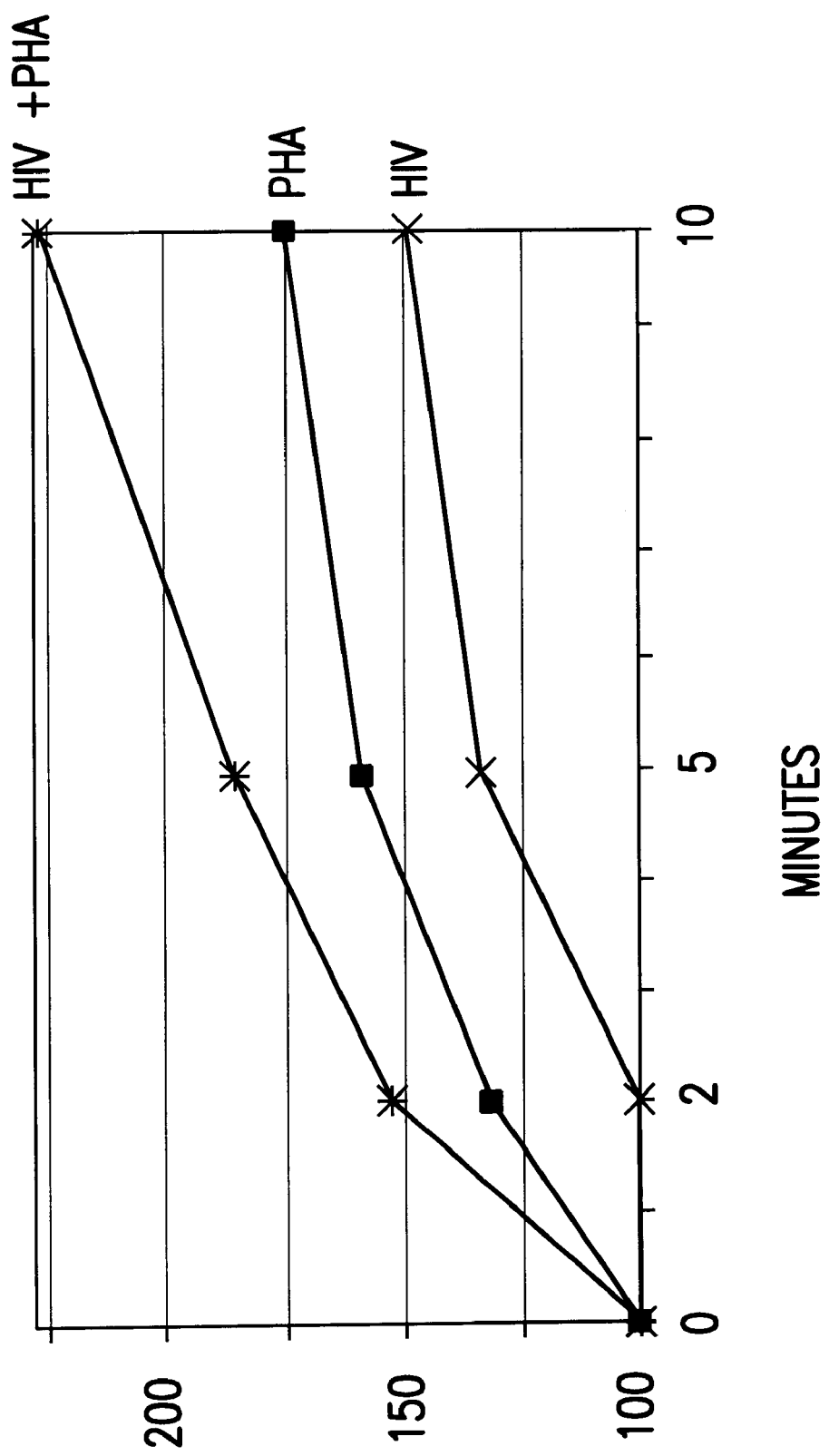
FIG. 2A is a photograph of a Western blot visualizing HIV-induced PTK activity in the early stages of cell activation.
Figure 2B:
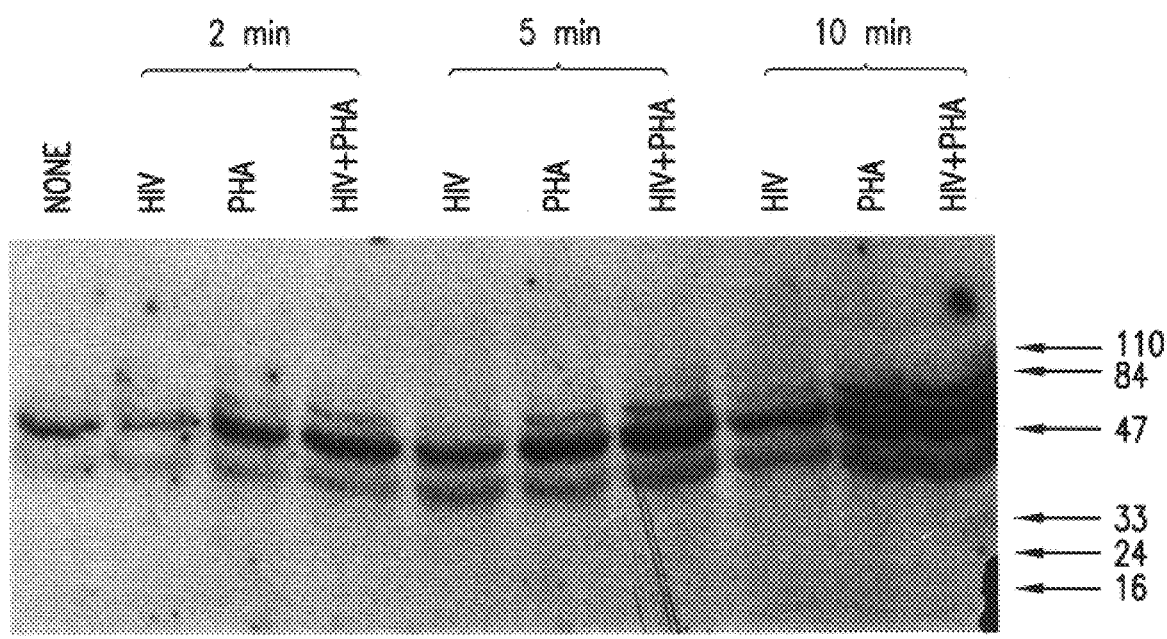
FIG. 2B is a quantitation graph depicting potentiation of the effect of PHA-induced phosphorylation of tyrosine resulting from pre-exposure of normal PBMC to HIV for 10 minutes before PHA stimulation as illustrated in FIG. 2A.

Normal PBMC were stimulated with HIV components or PHA, and tested for generation of phosphotyrosine after 0, 2, 5, and 10 minutes. Phosphotyrosine bands, measured on a Western blot as described above, were increased over background after 5 minutes of HIV component stimulation (FIGS. 2A and 2B). FIG. 2A shows the SDS-PAGE results directly; FIG. 2B is a graphic representation of the quantitated form of these results. Pre-exposure of normal PBMC to HIV components for 10 minutes before PHA stimulation potentiated the effect of PHA-induced phosphorylation of tyrosine (FIGS. 2A and 2B). This experiment demonstrates that the signal induced by HIV components in normal PBMC involves activation of PTK as part of the early activation events.

D. HIV Components Induce Phosphorylation of Tyrosine in Both CD4 and CD8 T-cells To investigate whether the CD4 molecule was necessary for the induction of PTK activity, enriched CD4 and CD8 T-cells were exposed to HIV. As stated above, because monoclonal antibodies to CD3, CD4 or CD8 receptors directly result in intracellular signaling, the usual methods for positive selection involving these antibodies could not be used.

CD4 and CD8 cells were purified by first E-rosetting T-cells (SRBC binds to the CD2 receptors but does not lead to signaling in the absence of a secondary stimulus). Subsequently, these E⁺-lymphocytes were depleted of either CD4 or CD8 T-cells to a purity of CD4 T-cells of 89% (±2%) with remaining CD8 of 3% (±1%) and CD8 T-cells of 76% (±3%) remaining CD4 of 19% (±2%). All purification procedures were performed at 4° C. to reduce activation caused by the purification procedure.

Figure 3:
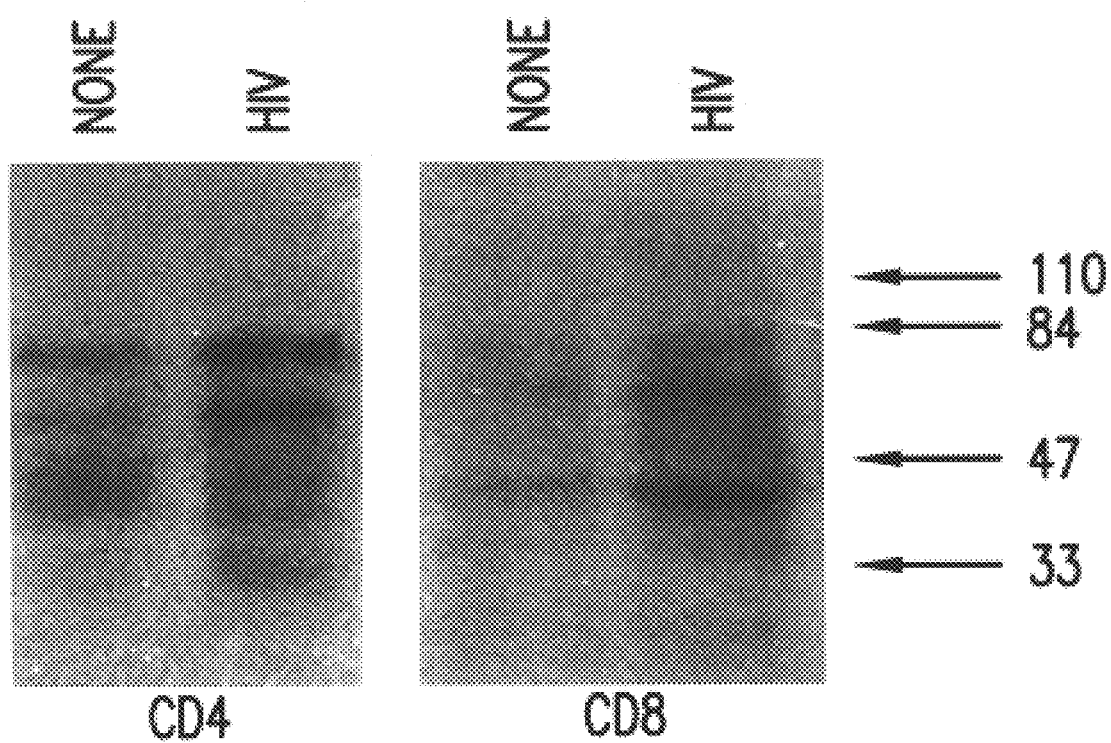
FIG. 3 is a half-tone photograph of a Western blot visualizing phosphorylated protein tyrosine residues as a result of induction of PTK activity by HIV components or PHA added to CD4 and CD8 cells in vitro.

HIV components induced phosphorylation of tyrosine residues in both CD4 and CD8 T-cells obtained in this way. In three experiments, exposure to HIV increased the intensity of the 40, 55, and 80 kD bands to 206±90% for CD4 cells and 181±20% for CD8 T-cells (FIG. 3). The experiment shows that the activation of PTK by HIV components is not mediated via the CD4 receptor. The finding is consistent with the above data showing that HIV components impaired the proliferation of both CD4 and CD8 T-cells.

E. HIV Components Induce an Increase in PKA Activity

Figure 4A:
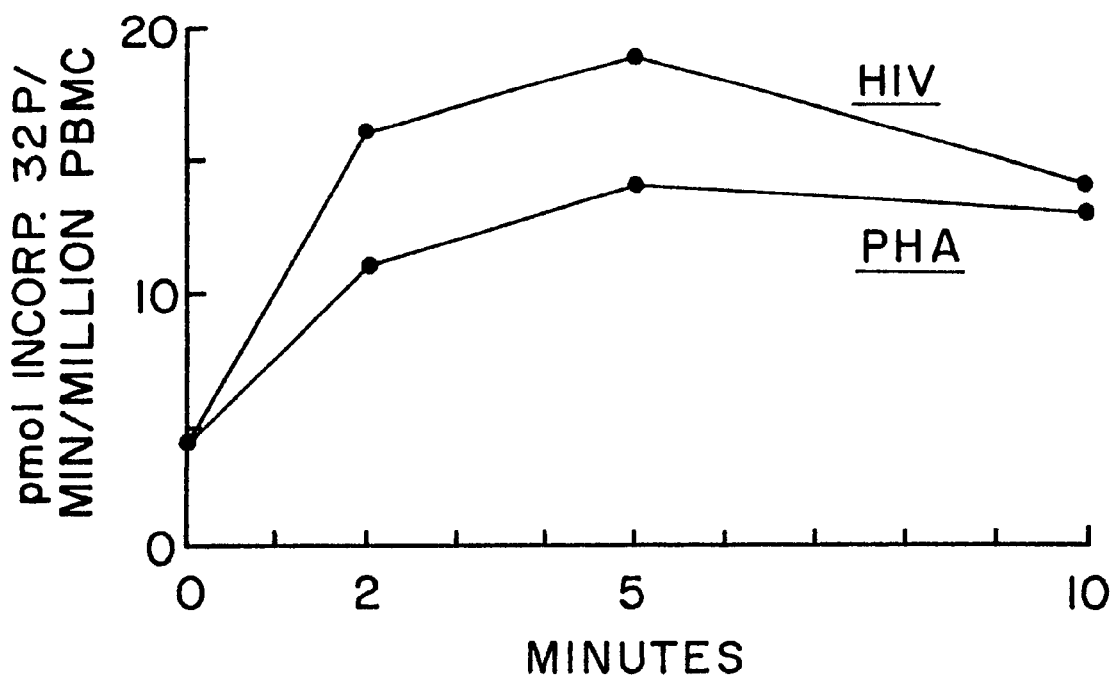
FIGS. 4(A–B) are graphs depicting an increase in total PKA activity resulting from addition of HIV components or PHA to normal PBMC.
Figure 4B:
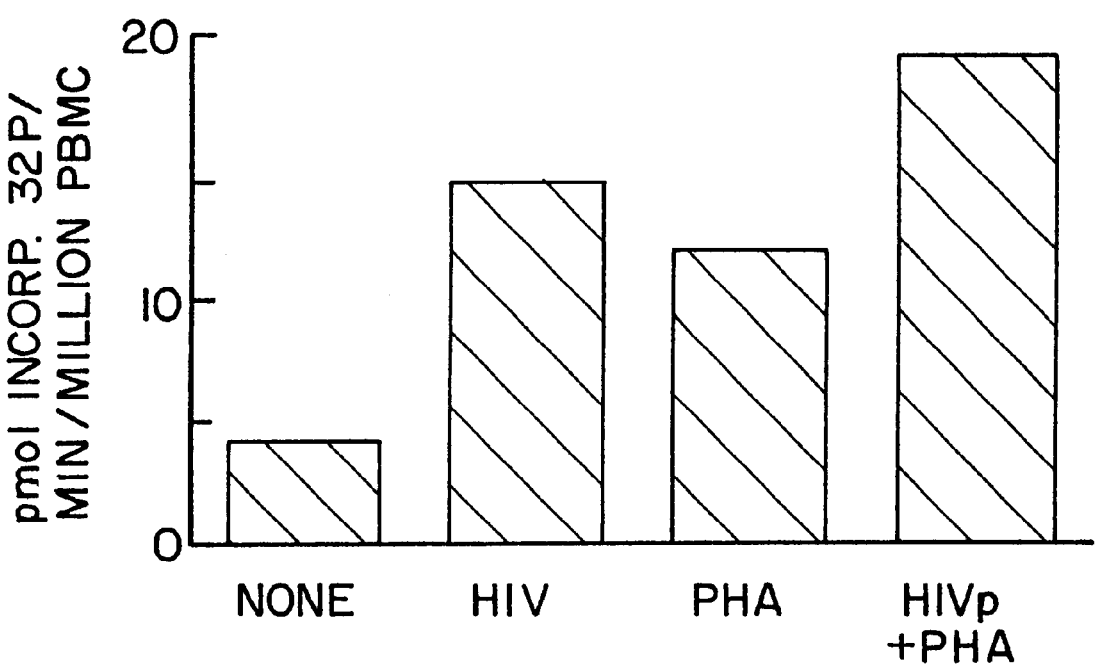

PKA is known to have an inhibitory effect on cell processes leading to proliferation. Addition of HIV components or PHA to normal PBMC induced an increase in PKA activity as measured by addition of specific PKA substrate to a cell lysate. Both HIV components and PHA induced increased PKA activity which reaches a maximum after 5 minutes of activation (FIG. 4A). Using five minute measurements, the induction of PKA activity by HIV components was confirmed in 4 of 4 experiments (see FIG. 4B). Preexposure of PBMC to HIV components for 10 minutes prior to PHA stimulation did not interfere with subsequent induction of PKA activity by PHA (see FIG. 4B).

About 70% of PBMC are T-cells and only T-cells respond to PHA. However, to eliminate the possibility that other cell subsets were responsible for the PKA activity, the experiment was repeated on carefully separated T-cells. Particular care was taken during separation to avoid endotoxin-containing media which may cause fluctuating preactivation. In three experiments, PKA activity increased from 2.5 (±1.0) to 10.0 (±1.6) nM $^{32}$P-incorporated/$10^6$ T-cells after HIV component stimulation and to 7.8 (±2.2) nM $^{32}$P/$10^6$ T-cells after activation with PHA. Thus, these results indicate that HIV components activate the inhibitory PKA pathway in T-lymphocytes.

F. HIV Components Introduce an Increase in Intracellular cAMP Concentration

Figure 5:
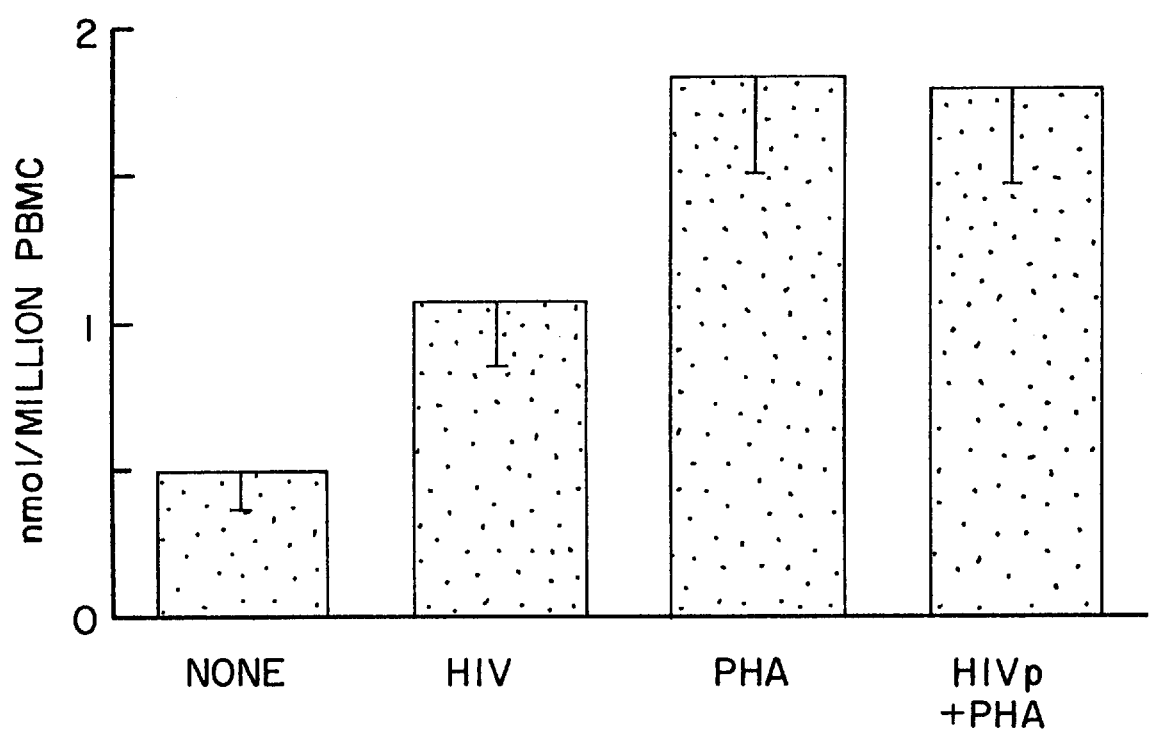
FIG. 5 is a graph depicting an increase in cAMP resulting from addition of HIV components or PHA to normal PBMC.

PKA is only active in the presence of cAMP; cAMP has also by itself an inhibitory effect on processes necessary for proliferation (Kammer, G. M., *Immunol Today* (1988) 9:277–279). Addition of HIV components or PHA to normal PBMC induced an immediate increase in cAMP as measured by RIA on cell lysates. The cAMP was increased in a time course which, although more donor-variable than the PKA time course, also reached a maximum after 2–5 minutes. The induction of cAMP by HIV components as shown in 5 of 5 experiments was set forth in FIG. 5. As shown in FIG. 5, the cAMP levels were increased from 0.5 nmol/$10^6$ PBMC to about 1 nmol/$10^6$ PBMC using HIV component stimulation alone and to about 1.8 nmol/$10^6$ PBMC either for PHA alone or for HIV components followed by PHA.

Carefully separated T-cells were also tested and showed similar results. In two experiments cAMP increased after addition of HIV components from 1.2 nmol/$10^6$ T-cells to 2.1 nmol/$10^6$ T-cells and from 2.8 nmol/$10^6$ T-cells to 4.0 nmol/$10^6$ T-cells. After activation by PHA, CAMP increased from 1.2 nmol/$10^6$ T-cells to 2.1 nmol/$10^6$ T-cells and from 2.8 nmol/$10^6$ T-cells to 8.3 nmol/$10^6$ T-cells.

The generation of cAMP in T-cells in response to HIV components confirms the above results showing activation of the inhibitory cAMP/PKA pathway.

G. Comparison of HIV Components with Cholera Toxoid in Their Ability to Induce cAMP/PKA To evaluate whether the increase in cAMP/PKA activity induced by HIV was comparable to changes seen in other systems, the increase was compared to the increase induced by Cholera toxoid. For Cholera toxoid, the impairment of PKC activity has been attributed to the increase in intracellular cAMP caused by the toxoid.

Specific cAMP dependent PKA activity induced by HIV components was 19 pmol/minute/10 PBMC compared to 16 pmol/minute/$10^6$ by Cholera toxoid. The level in nonstimulated cells was 6 pmol/min/$10^6$. The HIV-induced increase in cAMP activity is, therefore, of the same magnitude as Cholera toxoid.

H. Reagents that Increase Intracellular cAMP Impair Proliferation of Normal PBMC The role of cAMP in impairment of proliferation was demonstrated by adding Cholera toxoid or Br-cAMP (a stable form of cAMP) to cultures of normal PBMC. Both Cholera toxoid or Br-cAMP impaired PHA-induced cell proliferation as measured by $^3$H-thymidine uptake after 3 days of culture (Table 1). The 50% impairment of proliferation induced by HIV components is similar to the 50% impairment induced by 0.63 µg/ml of Cholera toxoid or 200 µg/ml of Br-cAMP. The experiment confirmed that cAMP impairs PHA-induced proliferation of T lymphocytes.

TABLE 1

| Reagent | Conc. | $^3$H-Thy. Incorp.[1] | Activity[2] |
|---|---|---|---|
| PHA | | 254.2 ± 9.0 | 100% |
| PHA + HIV[3] protein | | 122.0 ± 3.8 | 48% |
| PHA + Cholera toxoid[3] | | | |
| | 1.25 µg/ml | 84.6 ± 9.7 | 33% |
| | 0.63 µg/ml | 120.5 ± 9.2 | 47% |
| | 0.33 µg/ml | 168.7 ± 21.9 | 66% |
| PHA + Br-cAMP[3] | | | |
| | 400 µg/ml | 41.6 ± 2.1 | 16% |
| | 200 µg/ml | 96.3 ± 14.4 | 38% |
| | 100 µg/ml | 168.7 ± 21.9 | 66% |

[1]counts per minute (cpm) ×$10^{-6}$
[2]Activity expressed as percentage of activity of PHA control.
[3]HIV components, Cholera toxoid, and Br-cAMP do not stimulate
[3]$^3$H-thymidine uptake above background.

I. HIV Components Induce Membrane PKC Activity

PKC is present in the cytoplasm of resting lymphocytes and is translocated to the plasma membrane after activation. PKC activity is necessary for normal cell proliferation. Addition of PMA, a direct activator of PKC, to normal PBMC induced a lasting translocation of PKC to the cell membrane within the first two minutes of activation. PMA-induced PKC activity is independent of PKA activity.

Addition of HIV components or PHA to normal PBMC induced translocation of PKC to the cell membrane within the first two minutes of activation at 37° C. This initial membrane PKC activity decreased after 10 minutes. This increase/decrease in membrane PKC activity is similar to that which has been earlier reported for activation with other mitogens.

To investigate whether HIV component-induced membrane PKC activity was modified by cAMP/PKA, an inhibitor of PKA (H-89) was added to PBMC before simulation with HIV components. Addition of the inhibitor was associated with an increase in membrane PKC activity (Table 2) after activation with HIV as well as PHA.

TABLE 2

| | | Inhibitor | | |
|---|---|---|---|---|
| Cells* | none | (PTK) Tyrophostin-25 | (PKA) H-89 | Br-CAMP |
| Control | 1.3 ± 0.2 | 2.0 ± 0.9 | 6.0 ± 1.9 | 3.9 ± 1.7 |
| HIV | 3.0 ± 0.2 | 4.6 ± 0.0 | 12.9 ± 4.7 | 2.2 ± 1.5 |
| PHA | 4.2 ± 1.6 | 7.7 ± 7.7 | 9.4 ± 5.5 | 2.1 ± 1.6 |

*Cells were not stimulated (control) or were stimulates by HIV or PHA as indicated.

The results in Table 2 are given as nM of $^{32}$P/minute/$10^6$ PBMC as a measure of PKC membrane activity. cAMP/PKA activity therefore apparently plays a role in adjustment of the HIV component-induced membrane PKC activity.

J. HIV Impairs Subsequent PHA-Induced Membrane Translocation of PKC

Figure 6A:
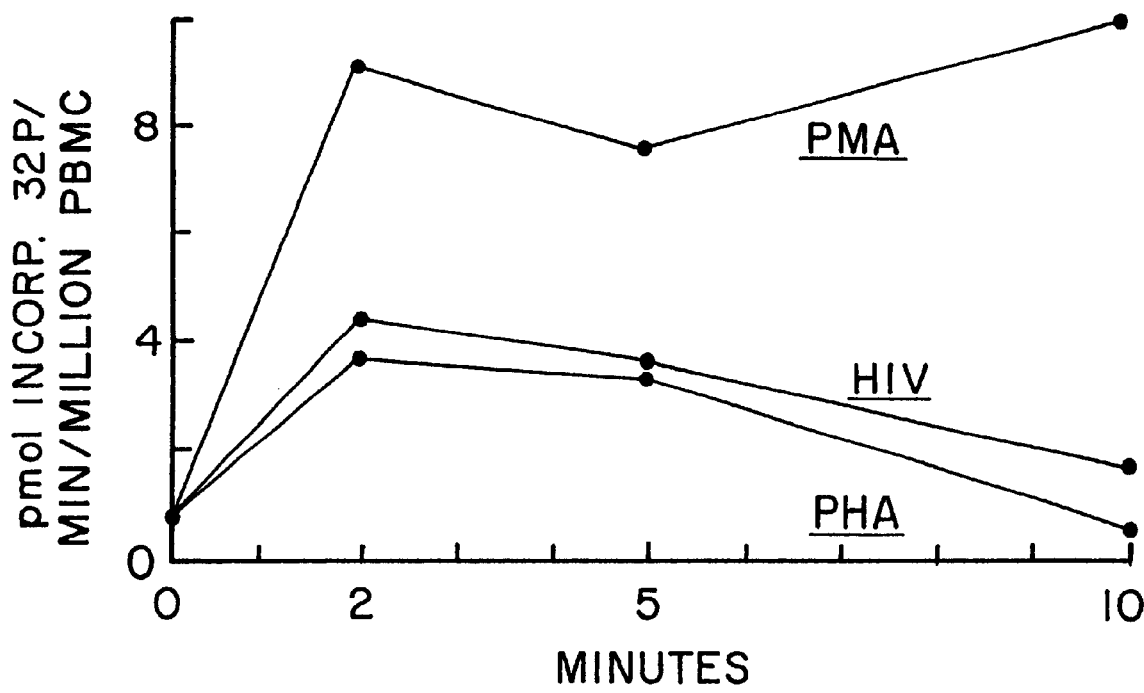
FIGS. 6A and 6B are graphs showing that addition of HIV components to normal PBMC results in decreased membrane PKC when subsequently activated with PHA or PMA.
Figure 6B:
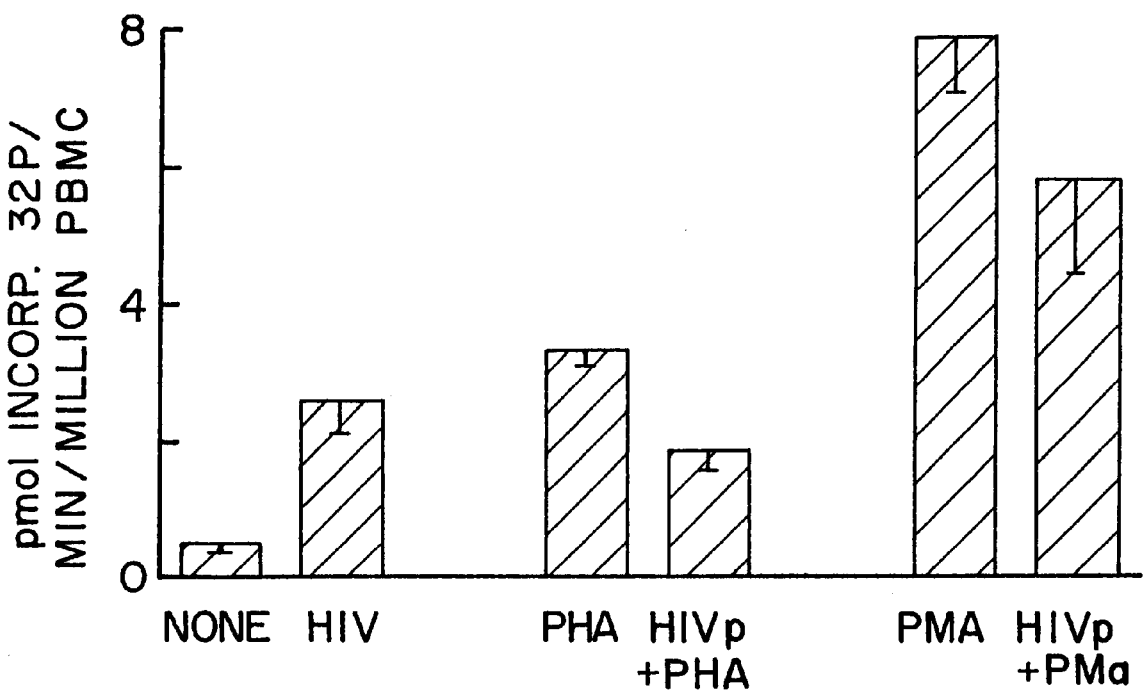

To determine whether signals induced by HIV components alter the lymphocyte's ability subsequently to become activated with PHA, normal PBMC were preexposed to HIV components for 10 minutes prior to 5 minutes of PHA activation. The PHA-induced membrane PKC activity obtained after preexposure to HIV components was clearly lower than with PHA induction alone. When the cells were stimulated by direct PKC activator PMA, pretreatment with HIV components had less and more variable effects. This shows that HIV component-induced signals reduce subsequent induction of membrane PKC activity in normal PBMC (normal PKC activity is necessary for normal cell proliferation). These results are shown in FIGS. 6A and 6B.

Figure 7:
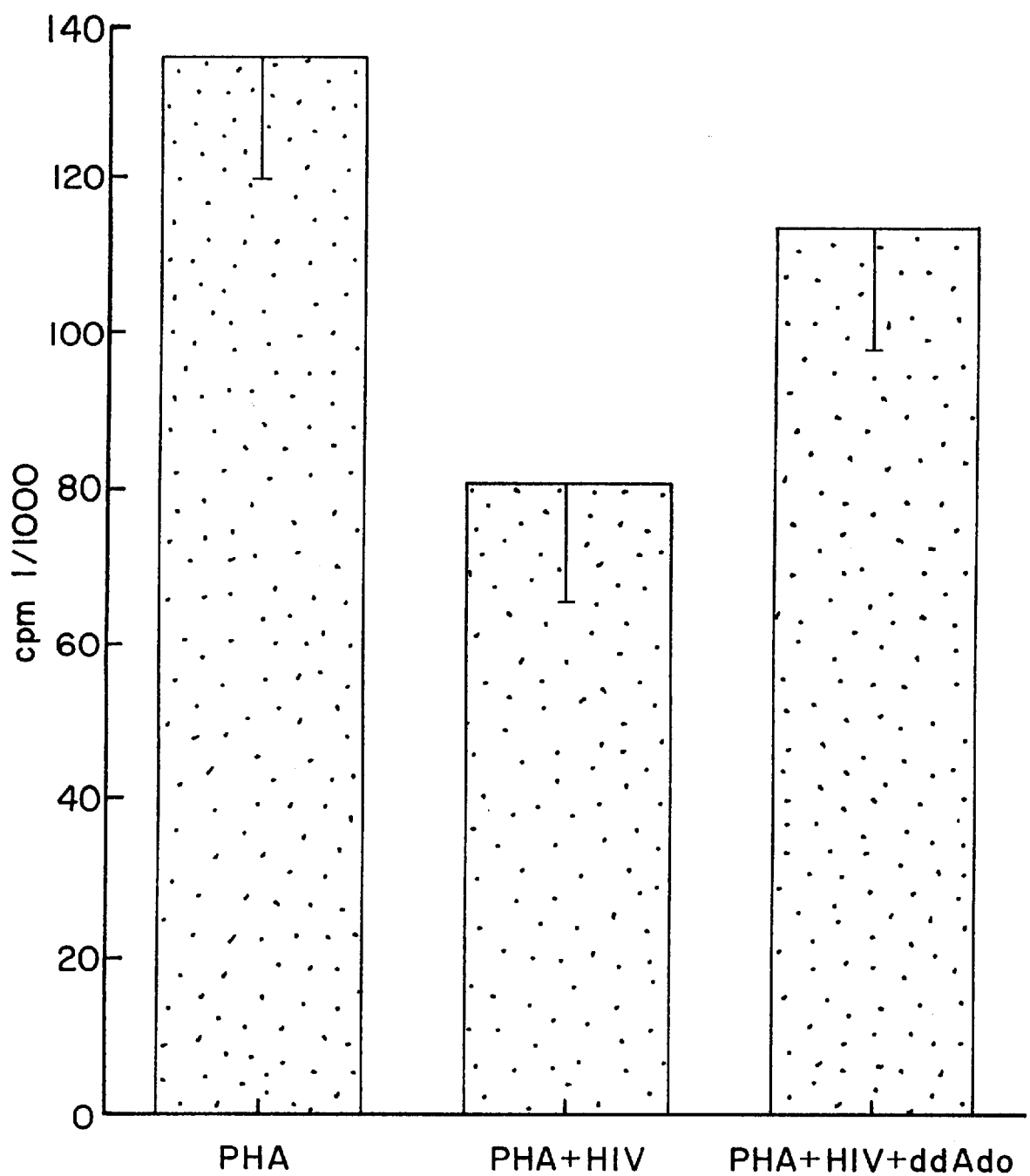
FIG. 7 shows the ability of ddAdo to restore the proliferative response of T-lymphocytes in response to stimulation by PHA after preincubation with HIV components.

K. Blocking of Intracellular cAMP Generation Reverses the Effect of HIV Components on T Lymphocyte Proliferation HIV components were added to PBMC for 1 hour followed by washing and then treating the cells with dideoxyadenosine (ddAdo) for 10 minutes, again followed by washing. Under these circumstances, the proliferative response to PHA could be restored (FIG. 7). This effect of ddAdo was seen in 5 of 5 experiments. The addition of ddAdo without HIV component treatment had a variable effect on the response to PHA.

Example II

Restoration of T-cell Function in HIV Infection By Reduction of Intracellular cAMP A. HIV Seropositive Subjects Have Elevated Levels of cAMP and PKA in Their PBMC and T-Cells To investigate whether increased cAMP/PKA activity could explain the decreased T-cell function in HIV infected individuals, a group of individuals who had been HIV seropositive for five or more years but were free of AIDS were investigated. cAMP levels were measured in resting peripheral blood mononuclear cells (PBMC) from 28 asymptomatic HIV seropositive homosexual men with established infection and was compared with 14 seronegative men from the same cohort and were found to be four times higher. (FIG. 8A)

T-cells compose 70% of PBMC, and CAMP levels in purified T-cells showed the same levels as in PBMC; extra care was taken to avoid fluctuation in resting CAMP levels during separation. In particular, all media were screened for endotoxin and only endotoxin/free propylene plastic ware was used. T-cells isolated from 11 HIV seropositive subjects showed a mean level of 2.40 ($\pm$0.5) pmol cAMP/$10^6$ cells compared to 2.2 ($\pm$0.4) pmol cAMP/$10^6$ cells in PBMC from the same individuals.

Figure 8B:
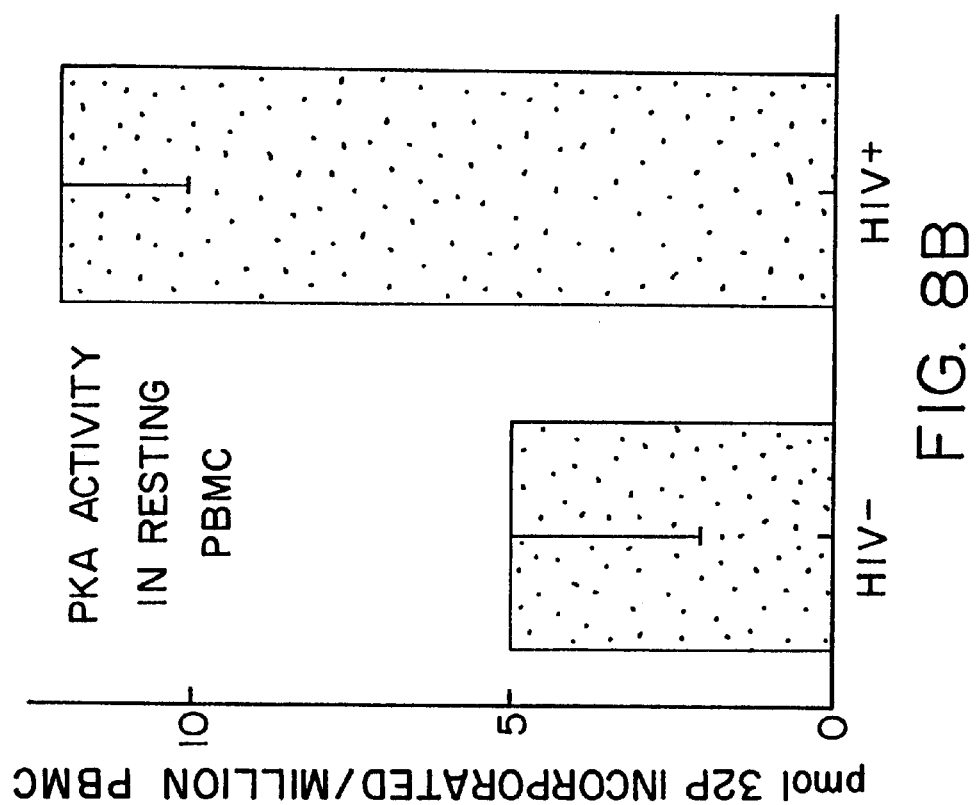
FIG. 8B is a graph depicting cAMP-dependent PKA activity in resting PBMC from HIV seropositive and seronegative subjects.
Figure 8A:
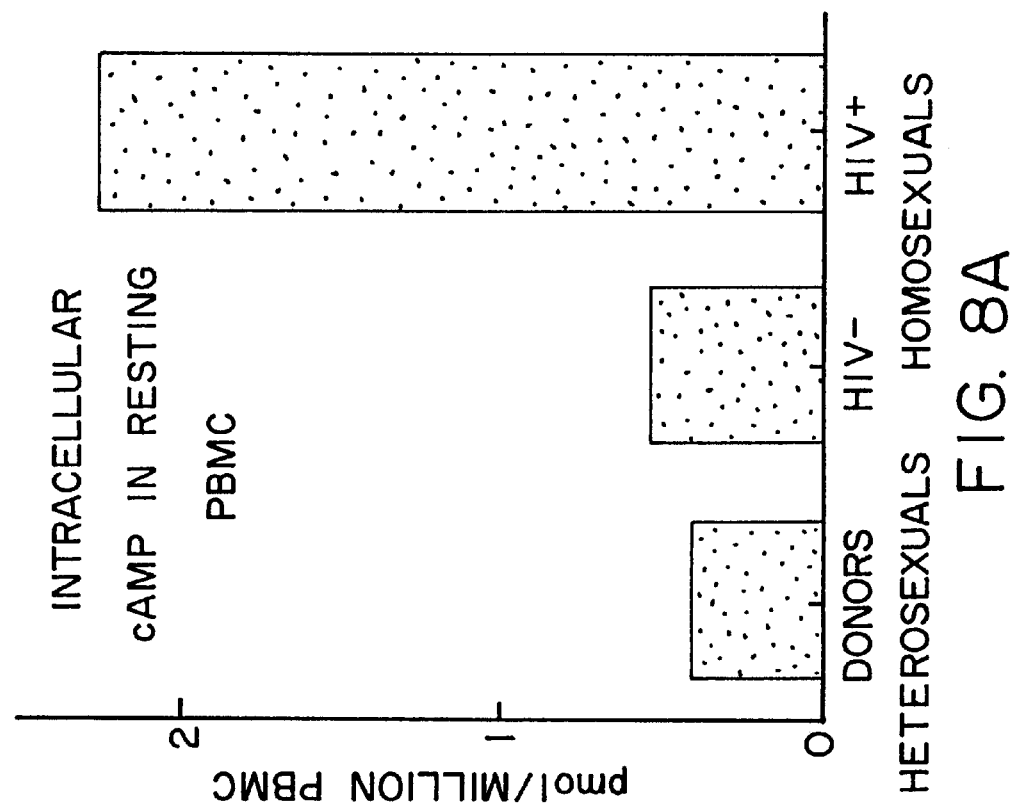
FIG. 8A is a graph depicting cAMP levels in resting PBMC from HIV seropositive and seronegative subjects.

Resting activity of cAMP-dependent PKA reflected the cAMP levels and showed two times higher mean value in PBMC from HIV seropositive subjects as compared to controls (FIG. 8B). Resting PKA levels measured in T-cells from eight separate HIV seropositive subjects showed 8.7 ($\pm$1.8) pmol PKA/$10^6$ PBMC, compared to 5.8 ($\pm$2.0) pmol PKA/$10^6$ cells in controls.

The difference between HIV seropositive and HIV seronegative subjects was significant (p=0.0005, Mann-Whitney). The mean CD4 T-cell number for HIV seropositive was 399$\pm$91$\times 10^6$/L (mean and SEM) and ranged from 43 to 1091$\times 10^6$/L.

cAMP-dependent PKA activity was measured in resting PBMC from six HIV seropositive homosexual men and compared with six HIV seronegative men from the same cohort. The difference between HIV seropositive and seronegative subjects is significant, P=0.05. Specific PKA activity was determined with a kit from Gibco following the manufacturer's protocol as the difference between phosphorylation of a PKA-specific substrate with and without a specific PKA inhibitor present. The PKA substrate was the synthetic peptide leu-arg-arg-ala-ser-leu-gly (SEQ ID NO:1) also called "kemptide". The specific PKA inhibitor was a synthetic peptide called PK1 which has an alanine to serine replacement in the consensus sequence: X-Arg-Arg-X-Ser-X where X (SEQ ID NO:2) is any amino acid which specifically binds to the pseudo-substrate region of the regulatory domain of PKA. The reaction mixture was spotted on cellulose paper disks and counted in a liquid scintillation $\beta$ counter.

B. PHA-Induced PKC Membrane Activity Is Decreased in PBMC from HIV Seropositive Subjects Membrane PKC activity of PMBC from HIV seropositive subjects was found to be less than a third of the activity from in HIV seronegative controls after PHA stimulation. Measurements of membrane PKC activities in HIV seropositive subjects increased only from mean 0.1 ($\pm$0.1) to 0.8 ($\pm$0.4) pmol 32p-incorporated/minute/million PBMC after PHA stimulation (N=4). In contrast, controls increased from 0.3 ($\pm$0.2) to 2.7 ($\pm$1.1) (N=3). (PKC was assayed from a kit from Gibco following the manufacturer's protocol.)

C. Inhibitors of Adenylate Cyclase Reduces cAMP Levels

The compound 2',5' dideoxyadenosine (ddAdo) inhibits adenylate cyclase, the enzyme responsible for the generation of cAMP, by competition for the "P"-binding site (Johnson, *J Biochem* (1990) 265:11595–11600). In contrast to 2',3'-adenosine analogs, ddAdo has no antiviral effect (Nishanian, Personal Communication). Addition of ddAdo to PBMC from HIV seropositive subjects for 10 minutes followed by washing resulted in lasting reduction of cAMP levels. In one such experiment (FIG. 9A), the intracellular cAMP level decreased to normal levels within 4 hours and remained at this level when tested after 20 hours. The effect of ddAdo was compared with two other adenylate cyclase inhibitors which are naturally occurring adenosine phosphates. When used in equal concentrations, the three inhibitors gave similar reductions in intracellular CAMP levels. For example, when added in 10 ng/ml for 10 min, ddAdo decreased the CAMP levels from 5.3 pmol/$10^6$ PBMC to 3.6; 3' AMP to 3.5; and 2',3'deoxy-AMP reduced the level to 3.2 pmol/$10^6$ PBMC.

Figure 9B:
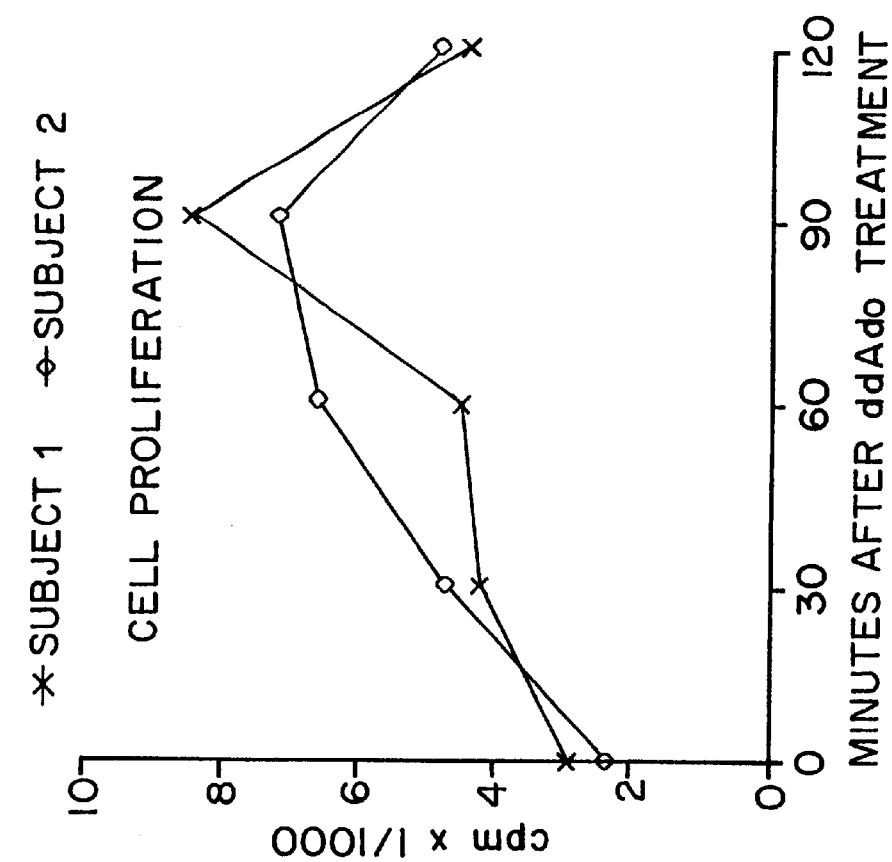
FIG. 9B is a graph showing the increase in proliferation of PBMC from an HIV seropositive subject in response to *Candida albicans* after ddAdo treatment.
Figure 9A:
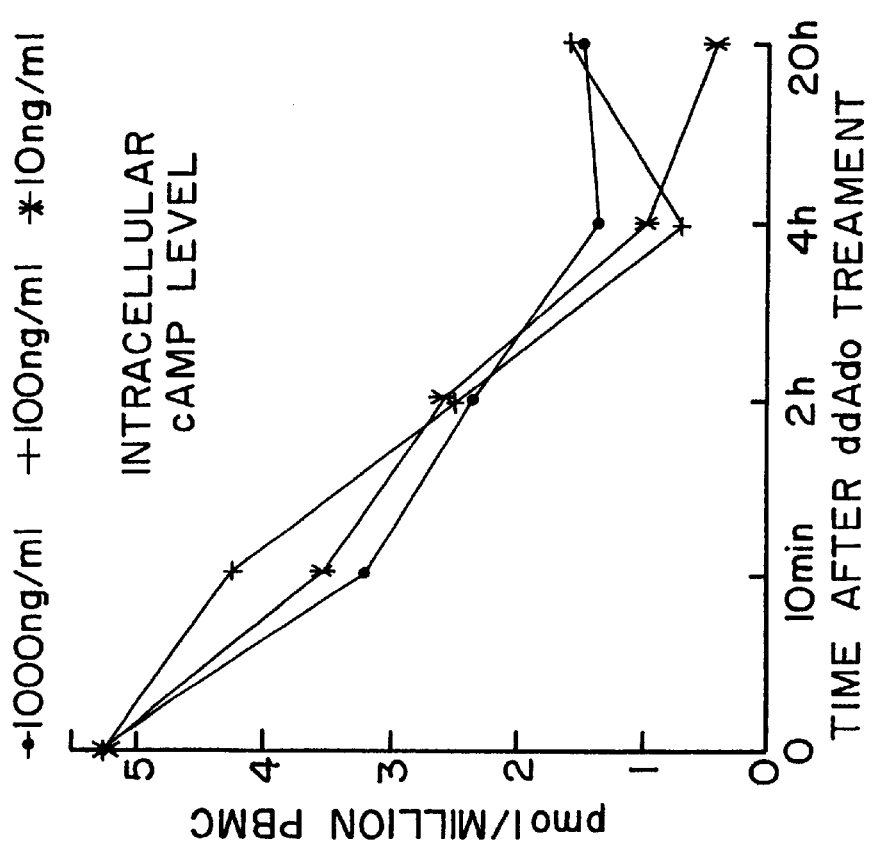
FIG. 9A is a graph showing that treatment with dideoxyadenosine (ddAdo) of PBMC from HIV seropositive subjects results in a lasting reduction of cAMP.

FIG. 9B shows proliferative response to *Candida albicans* after ddAdo treatment in two subjects selected to have a major increase in proliferation. PBMC from 2 HIV seropositive subjects were pulsed with ddAdo for 10 minutes, washed and then stimulated with the recall antigen *Candida Albicans* 30, 60, 90 and 120 minutes after ddAdo treatment.

Intracellular cAMP levels and proliferative responses to *Candida albicans* tended to be inversely correlated one hour after ddAdo treatment in 11 HIV seropositive subjects (Kendal rank correlation, tau –0.46, p<0.07). However, there was no correlation between initial levels of cAMP and initial proliferative responses (Kendal rank correlation, tau –0.15), mainly because the initial proliferative responses in HIV seropositive subjects were lacking or low.

cAMP was determined using a commercial scintillation proximity RIA (Amersham, Arlington Heights, Ill.) following the manufacturer's protocol. PKA activity was determined using a kit from Gibco (Grand Island, N.Y.) and the manufacturer's protocol. For the cAMP assay, cells were lysed and sonicated in assay buffer (provided with the kits). Proliferative assays were performed as described above.

D. Administration of ddAdo Restores T-Cell Function

To inquire into whether the reduction of intracellular cAMP by ddAdo would restore T-cell function, proliferative responses of PBMC from HIV seropositive subjects to a specific recall antigen (*Candida albicans*) were increased by ddAdo in concentrations ranging from 6 to 20 ng/ml. Higher concentrations of ddAdo were found to be suppressive and lower concentrations were not active. ddAdo, therefore, seems to work within a "therapeutic window."

Proliferative assays were done in triplicates of 50,000 PBMC in 200 $\mu$L RPMI with 10% FCS and 8 $\mu$g/ml of *Candida albicans*. ddAdo was added in two-fold dilutions; tritiated thymidine was added at day 5 and cells were harvested at day 6. Concentrations of ddAdo from 12.5 to 50 ng/ml gave the highest responses. The results for an effector target ratio of 6:1 are shown in FIG. 10B, but other ratios showed similar results. Ratio 1:12 gave 48% ($\pm$12) without and 76% ($\pm$9) with ddAdo during priming. Ratio 1:25 gave 61% ($\pm$15) without and 77% ($\pm$9) with ddAdo.

In each of four separate experiments, the initial percentages of target lysis in HIV seronegative subjects were higher than those in seropositive subjects except for one HIV seropositive. ddAdo had minimal effect on HIV seronegative cells. The responses to Candida albicans in all 14 HIV seropositive subjects tested were increased from 2900 (±1300) cpm (mean and SEM) to 6100 (±1600) cpm compared with 6600 (±2000) cpm in seven HIV seronegative controls from the same cohort (addition of ddAdo to controls gave 7600 (±1.9) cpm). Most impressive were the findings that some HIV seropositive subjects increased from less than 1000 cpm to about 10,000 cpm (FIG. 10A). Impaired responses to PHA were also improved by ddAdo.

Cytotoxic T-cells from HIV seropositive subjects "regained" their normal ability to lyse allogenic tumor cell line in the presence of ddAdo as shown in FIG. 10B. In this experiment, ddAdo was added either during the six days of generation/priming (middle column of FIG. 10B) or during the three hour cytotoxic assay (right column of FIG. 10B). The cytotoxic assay used was a standard assay. Briefly, $10^6$ PBMC were primed and irradiated (3000 Rad) Raji B-lymphoblastoid cells (8:1 ratio) for six days and added to triplicates of $^{51}Cr$-labeled target Raji cells in effector target ratios from 6.25 to 50. $^{51}Cr$ released to the supernatant was measured in a gamma counter. Percentage of specific $^{51}Cr$-release was calculated as 100×(released by PBMC–spontaneous release)/(maximum release with Triton X–spontaneous release). ddAdo was added in concentrations of 10 or 100 ng/ml either during priming or lysis.

Immunoglobulin production by B-cells is regulated by T-cells; CD4 provides "help" for de novo synthesis and CD8 suppresses immunoglobulin production. In HIV infection, increased total immunoglobulin production with a decrease in certain specific HIV antibodies to HIV GAG proteins during infection is a common finding (Lange, et al. *AIDS* (1987) 1:155–9). In this experiment, $10^6$ PBMC from HIV seropositive donors were incubated in 1 ml cultures with and without ddAdo (1–100 ng/ml) for 10 days. IgG and anti-HIV antibodies in supernatant were measured by ELISA. p24 binding capacity was measured with a kit from DuPont following the manufacturer's protocol. Addition of ddAdo to cultures of PBMC from HIV seropositive subjects restored production of specific antibodies to p24 (Table 3). An effect of ddAdo on T-cells has been shown above but a possible direct effect on B-cells cannot be ruled out.

TABLE 3

Effect of ddAdo on the Production of HIV Specific Antibodies

| Patient/ Addition: | IgG (µg/ml) | Anti-HIV Ab (OD) | p24 Binding Capacity (pg/ml) |
|---|---|---|---|
| 1 none | 326 | .5910 | 0 |
| +ddAdo | 367 | .5300 | 14 |
| 2 none | 98 | .1320 | 0 |
| ++ddAdo | 89 | .1940 | 16 |
| 3 none | 366 | 1.1390 | 0 |
| ++ddAdo | 309 | 1.0820 | 88 |
| 4 none | 123 | .2000 | 25 |
| ++ddAdo | 142 | .1640 | 49 |
| 5 none | 55 | .1480 | 41 |
| ++ddAdo | 192 | .1360 | 32 |
| 6 none | 76 | .0330 | 60 |
| ++ddAdo | 80 | .0330 | 50 |
| 7 none | 244 | .0570 | 376 |
| ++ddAdo | 145 | .2990 | 418 |
| 8 none | 143 | .4860 | 1540 |
| ++ddAdo | 170 | .3900 | 1560 |

Figure 11:
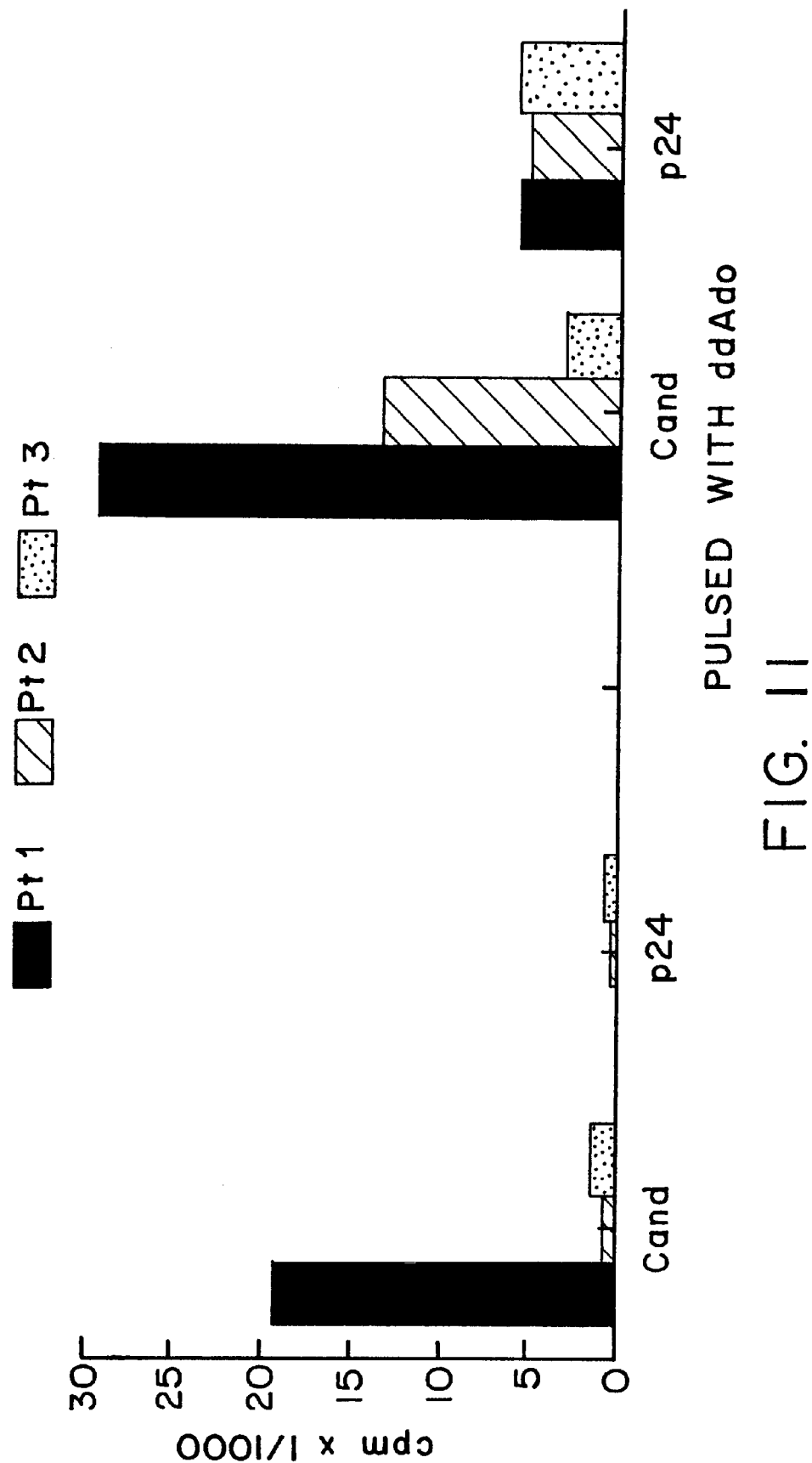
FIG. 11 is a graph showing T lymphocyte proliferative response in HIV seropositive subjects to a specific recall antigen (*Candida albicans*) and to an HIV-specific protein (p24) before and after ddAdo treatment.

Addition of ddAdo to cultures of PBMC from HIV seropositive subjects increased spontaneous anti-p24 antibodies in individuals with none/low spontaneous production (p24 is an HIV core protein). One million PBMC from HIV seropositive donors were incubated in 1 ml cultures with and without ddAdo (1–100 ng/ml) for 10 days. IgG10 and production of anti-HIV antibodies to p24 in supernatants were measured by ELISA. p24 binding capacity was measured with a kit from DuPont (Delaware) following the manufacturer's protocol.

ddAdo also restores/increases T lymphocyte responses in HIV seropositive subjects directed against HIV and may, therefore, help fight the virus (FIG. 11).

Thus, reduction of abnormal cAMP levels significantly restored both cellular and humoral responses in HIV infection. Three different compounds were shown to decrease cAMP levels in cells from HIV infected patients. Clonal expansion of T-cells is a prerequisite for normalization of immune function in HIV infection.

E. Dan-Shen Extract Lowers Intracellular cAMP Levels in PBMC from HIV+ Subjects

Dan-shen radix (22 g) was powdered and extracted with methanol (40 ml) two times at 50° C. Methanol extract was diluted with distilled water (approximately 30 ml) and extracted with chloroform. The upper methanol $H_2O$ phase was further extracted with ethyl acetate (50 ml). Ethyl acetate solution was successively extracted with chloroform (1×, 15 ml) and water (3 times). Ethylacetate was evaporated under vacuum. The isolated yellowish resin line material (approximately 150 mg) was dissolved in 15 ml $H_2O$. It showed inhibitory activity against adenylate cyclase.

Further purification was achieved by reverse phase chromatography. 3 ml of above solution was applied on $C_{18}$ Sep-Pak cartridge (Waters) equilibrated with water+0.1% TFA. The column was washed with $H_2O$-TFA until absorbance at 280nm reached baseline. Bound material was eluted from the column by stepwise elution with $H_2O$-acetonitrile-TFA mixtures. There were three peaks on elution curve at 20%, 40% and 70% acetonitrile. The effluent from the above step was rechromatographed again on $C_{18}$ cartridge and yielded additional quantities of the three products. All fractions had inhibitory activity against adenylate cyclase, but the most active was Fraction 2 eluted with 40% acetonitrile. Fraction 2 was added in various PBS dilutions to lymphocytes from HIV seropositive subjects. cAMP was then measured on lysates of these cells after 1 hour.

Figure 12A:
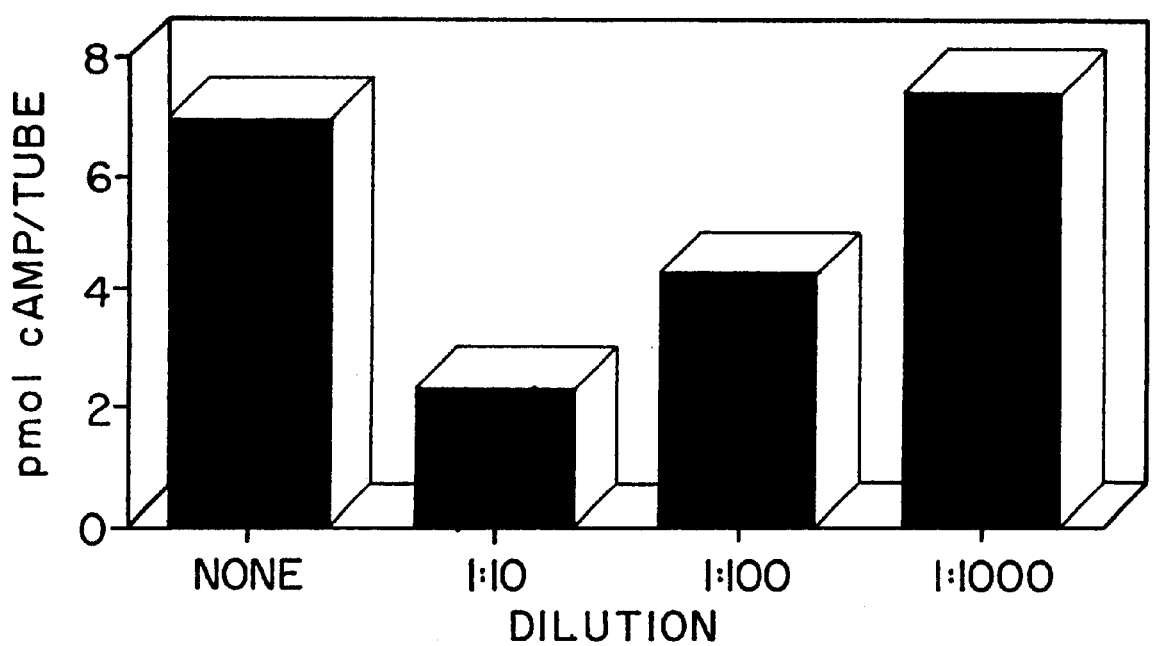
FIG. 12A is a graph depicting the effect of dan-shen water extract on intracellular cAMP levels in PBMC from an HIV seropositive subject.
Figure 12B:
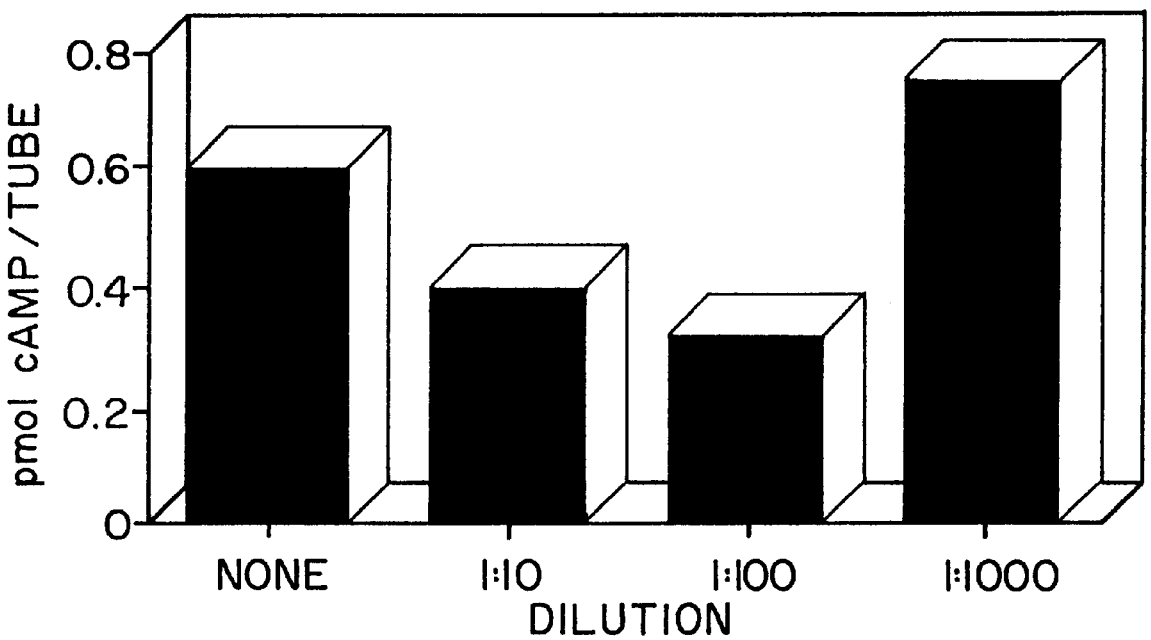
FIG. 12B is a graph depicting the effect of purified dan-shen extract on intracellular cAMP levels in this system.

Both a boiling water extract and the partially purified fraction described above were tested. The results are shown in FIGS. 12A and 12B, respectively. As shown in FIG. 12A, in the absence of dan-shen water extract, the measured levels of cAMP were approximately 7 pmol/sample. Dan-shen extract reduced these levels in a dose-dependent fashion; at a 1:1 dilution the level fell to 2.3 pmol; at a 1:10 dilution, 24.3 pmol/sample; and at a 1:100 dilution there was no effect on the cAMP level. FIG. 12B shows a reduction from 0.6 pmol per sample in the absence of partially purified extract to 0.4 pmole for the 1:10 dilution and to 0.3 pmol for the 1:100 dilution. The 1:1000 dilution shows no effect.

Figure 13:
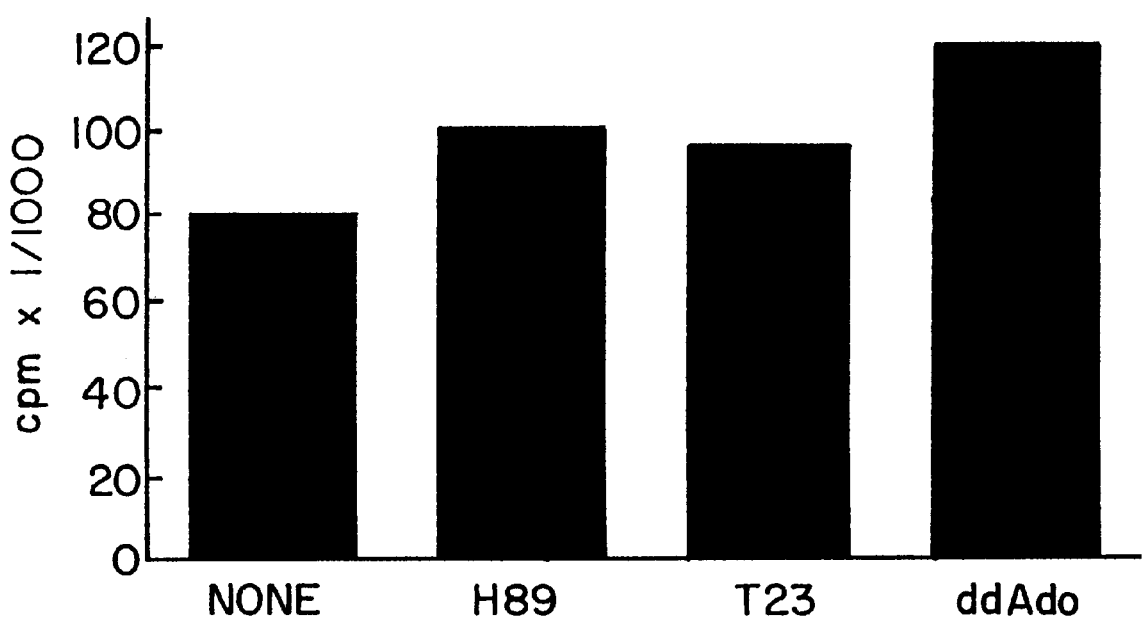
FIG. 13 is a graph showing the effect of various inhibitors on the proliferative response to PHA of PBMC from an HIV seropositive subject.

F. Administration of Inhibitors of PKA or PTKs Increases or Restores T-Cell Function FIG. 13 shows that an inhibitor of PKA, H-89, and an inhibitor of PTKs, T-23, enhance proliferation of PBMC from an HIV seropositive subject to the mitogen PHA. These results show that lymphoid cell function may be restored by inhibiting other components in the PKA/cAMP inhibitory pathway in addition to adenylate cyclase.

What is claimed is:

1. A method for preventing or reversing the functional deficiency induced in lymphoid cells during HIV infection or by exposure to HIV components, which method comprises inhibiting the cAMP/PKA pathway of said cells by contacting said cells with an amount of 2',5'-dideoxyadenosine (ddAdo) effective to inhibit adenylate cyclase in said cells.

2. A method to treat a subject infected with HIV, which method comprises administering to said subject an amount of 2',5'-dideoxyadenosine (ddAdo) effective to inhibit the PKA/cAMP pathway in the lymphoid cells of said subject.

3. The method of claim 2 wherein administering is conducted in vivo.

4. The method of claim 2 wherein said administering is conducted extracorporeally.

5. The method of claim 2 which further includes administering to said subject an effective amount of an antiviral agent.

6. The method of claim 5 wherein the antiviral agent is selected from the group consisting of AZT, ddI and ddC.

7. A pharmaceutical composition useful for reversing the negative effect of exposure to HIV components on lymphoid cell function, which composition comprises an effective amount of 2',5'-dideoxyadenosine (ddAdo) in admixture with at least one pharmaceutically acceptable excipient which further contains an antiviral agent.

8. The composition of claim 7 wherein the antiviral agent is selected from the group consisting of AZT, ddI and ddC.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO: 1:

Leu Arg Arg Ala Ser Leu Gly
1               5

(2) INFORMATION FOR SEQ ID NO: 2:

(i) SEQUENCE CHARACTERISTICS:
       (A) LENGTH: 6 amino acids
       (B) TYPE: amino acid
       (C) STRANDEDNESS: single
       (D) TOPOLOGY: linear (xi) SEQUENCE DESCRIPTION: SEQ ID NO: 2:

Xaa Arg Arg Xaa Ser Xaa
1               5